(12) United States Patent
Colin et al.

(10) Patent No.: US 6,686,195 B1
(45) Date of Patent: Feb. 3, 2004

(54) METHOD AND APPARATUS FOR ULTRASONIC LYSIS OF BIOLOGICAL CELLS

(75) Inventors: Bruno Colin, Marcy l'Etoile (FR); Philippe Cleuziat, Lyons (FR); Patrick Broyer, Villeurbanne (FR); Claude Mabilat, Saint Germain au Mont d'or (FR); Sandra Incardona, Lyons (FR)

(73) Assignee: Biomerieux S.A., Marcy l'Etoile (FR)

( * ) Notice: Subject to any disclaimer, the term of this patent is extended or adjusted under 35 U.S.C. 154(b) by 0 days.

(21) Appl. No.: 09/937,992
(22) PCT Filed: Apr. 3, 2000
(86) PCT No.: PCT/FR00/00832
§ 371 (c)(1), (2), (4) Date: Dec. 13, 2001
(87) PCT Pub. No.: WO00/60049
PCT Pub. Date: Oct. 12, 2000

(30) Foreign Application Priority Data

Apr. 1, 1999 (FR) .............................................. 99 04289

(51) Int. Cl.⁷ ................................................ C12M 1/33
(52) U.S. Cl. ................................ 435/306.1; 435/286.7; 435/173.7; 422/20; 366/110; 366/113
(58) Field of Search ........................... 435/286.7, 288.1, 435/173.7, 304.1, 306.1; 422/128, 20; 366/31, 110, 113

(56) References Cited

U.S. PATENT DOCUMENTS

| | | | | |
|---|---|---|---|---|
| 5,247,924 A | * | 9/1993 | Suzuki et al. ................... | 601/4 |
| 5,962,338 A | * | 10/1999 | Sucholeiki .................. | 436/518 |
| 6,071,480 A | * | 6/2000 | Halaka ....................... | 422/128 |
| 6,100,084 A | * | 8/2000 | Miles et al. .............. | 435/306.1 |
| 6,418,084 B2 | * | 7/2002 | Saito et al. .................. | 367/152 |

FOREIGN PATENT DOCUMENTS

| | | |
|---|---|---|
| EP | 0 271 448 | 6/1988 |
| EP | 0 337 690 | 10/1989 |
| EP | 0 604 742 | 7/1994 |
| EP | 0 769 475 | 4/1997 |
| GB | 938 163 | 10/1963 |

* cited by examiner

Primary Examiner—David A. Redding
(74) Attorney, Agent, or Firm—James C. Lydon

(57) ABSTRACT

An apparatus including at least one sonotrode (2) designed to generate ultrasound of variable power in at least one biological sample (5) containing cells to be lysed, the sample (5) being contained in at least one receptacle (4 or 10) such that the sonotrode (2) is in direct contact with the receptacle (s) (4). Also disclosed is a method for using ultrasound to lyse a biological sample (5) contained in a receptacle (4), which includes placing the receptacle (4) in direct contact with the sonotrode (2), and activating the sonotrode (2) for long enough to lyse the cells in the sample (5) but preserve the DNA and/or RNA molecules released for subsequent operations, e.g. amplification. The invention is particularly applicable in the discipline of molecular biology.

13 Claims, 4 Drawing Sheets

METHOD AND APPARATUS FOR ULTRASONIC LYSIS OF BIOLOGICAL CELLS

This application is a U.S. National Stage of International application PCT/FR00/00832, filed Apr. 3, 2000 and published on Oct. 12, 2000 in the French Language.

This invention concerns an apparatus and a method for generating ultrasound of variable power in a receptacle containing a sample to be lysed with or without the presence of glass beads. The frequency range of the ultrasound is between 20 and 50 kilohertz (kHz) approximately.

The background art essentially consists of two methods which use ultrasound to lyse microorganisms in biological applications. The first method involves direct sonication in which the sonotrode is submerged in the sample to be lysed. The principle exploited in this case consists in placing the sonotrode directly in contact with the liquid and generating high energy ultrasound in either a continuous fashion or in pulses to induce intense cavitation within the medium. In general, the sonotrodes used have a very high power output (100 to 1000 Watts [W]) and can be used to lyse a wide variety of different types of sample which are known to be relatively difficult to lyse in a short time (of the order of one minute).

However, two major problems restrict the utility of this method.

Firstly, since the phenomenon of cavitation is very difficult to control, the percentage lysis will not be reproducible across a large number of test runs.

Moreover, high-intensity cavitation induces heavy and uncontrolled nucleic acid fragmentation which can be a problem if the user is trying to detect and amplify in samples which only contain dozens or hundreds of microorganisms per microliter (i.e. very low densities).

Finally, since the sonotrode is in direct contact with the sample, this method cannot be used in the automated analysis of patients' samples unless a wash step for the said sonotrode is included-such wash steps are time-consuming and costly to implement in automatic analyzers.

There are also other disadvantages related to the above-mentioned problems. Firstly, cavitation induces condensation of part of the sample which further compromises the resolution of the test being performed. Finally, if the acoustic power is too great, excessive heating of the tube can lead to sample breakdown or even melting of the said tube.

The second method involves bath sonication which is fully described in patent U.S. Pat. No. 5,374,522. The principle consists in using an ultrasound cleaning bath filled with water with the bottom of the tubes containing the samples to be lysed submerged therein.

The samples are exposed to an ultrasound field-usually constant—for about 15 minutes (min). Beads present in the tubes are thus induced to move around vigorously which causes them to collide with one another and create shear forces which are sufficient to lyse microorganisms. In contrast to the first method described above, this second method requires the use of glass beads to insure adequately efficient lysis. This second method bypasses certain of the problems mentioned in connection with the preceding direct sonication method.

Thus, with the samples being contained in a sealed tube, nthere is no contamination of the vibrating element since the ultrasound waves are transmitted through the water (which is an excellent medium for the propagation of such waves) from the bottom of the bath into the inside of the sample-containing tube.

Moreover, since the energy density (expressed in terms of Watts per milliliter [W/ml]) generated in the medium is about 300 times lower at the same frequency, there is less cavitation.

The major disadvantage of this method is the fact that it is difficult to automate because of the problems associated with the handling of liquids (the filling and emptying of the bath), because degassing is necessary before sonication and because of the complications after sonication associated with having to manipulate wet tubes (which tend to drip and compromise cleanliness).

There are further disadvantages. Thus, the results are not reproducible because the acoustic power is not the same in all parts of the receptacle placed in the bath for sonication. This is due to the way in which bath sonicators are constructed with one or more transducers below the tank. Thus, the ultrasound field generated by a transducer is not equivalent in all spatial dimensions. As a result, both the efficiency of lysis of microorganisms and the extent of nucleic acid fragmentation vary enormously between different samples, and this variation cannot be controlled.

There are, however, sonication methods based on the sonotrode being in direct contact with the biological sample to be lysed, e.g. Patent Application EP-A-0.337.690.

However, the contact between receptacle and sonotrode is constituted by a planar surface which is not compatible with homogenous lysis throughout the test sample. Such devices do not meet the lysate quality requirements necessary for the release of nucleic acids. The only solution to this is to increase the lysis time considerably—by a factor of at least two—with a concomitant increase in the risk of denaturation or even destruction of the nucleic acid molecules which receive the most intense fraction of this heterogeneous sonication.

A comparison of the energy densities (W/ml) gives an idea of the major differences which exist between the two methods of the background art described above. Energy density can be defined as the integral over time of the power delivered to the sample divided by the volume of the sample. This quantity can be experimentally determined by measuring the temperature rise over a given period of time (and the results for the two different methods can be compared).

$$E = \int_0^T \frac{W}{V} dt \text{ where } E: \text{ energy density.}$$

$W$: output power ($W$)

$V$: Sample volume (ml)

Measurements of the temperature inside the tubes after 15 min of bath sonication give an estimate of the power delivered into the sample:

$T_{0mn}$=21° C.

$T_{15mn}$=40.6° C.

i.e. $\Delta t$=19.6° C. and DW=$\Delta t$×0.3 ml=19.6×0.3=5.88 cal/15 min therefore Wt=(5.88×4.18)/(60×15)=0.027 W The energy density D (in W/ml) in a bath sonicator-type ultrasound bath is:

$D$=0.027/0.3=0.09 W/ml

It is apparent that the energy density is about three hundred times lower than that generated by a sonotrode directly submerged in the medium since, according to published data, the energy density in this case is generally at least 30 W. This value is confirmed by the data given in document U.S. Pat. No. 5,374,522 on bath sonication.

In accordance with this invention, the proposed apparatus provides a solution to all the above-mentioned problems in that it makes controlled nucleic acid fragmentation possible without broaching the integrity of the tube containing the sample. The entire unit remains perfectly clean because there is no contact between the outer surface of the tube and any liquid, the contents of said tube being entirely isolated from the exterior. This isolation precludes the possibility of any material being ejected out of the tube during sonication, and also considerably reduces evaporation and condensation.

To this effect, this invention concerns an apparatus which includes a sonotrode designed to generate ultrasound of variable power within at least one biological sample containing cells to be lysed, the sample(s) being contained in at least one receptacle suited for that purpose and the sonotrode being in direct contact with the receptacle(s) containing the cells to be lysed without any fluid between the said surfaces (of the sonotrode and of the receptacle), characterized in that the active surface of the sonotrode matches the shape of all or part of each receptacle containing the sample to be lysed; the active surface of the sonotrode which is in contact with the receptacle is concave in shape.

In another embodiment, the active surface of the sonotrode which is in contact with the receptacle is convex in shape.

When the active surface is convex in shape, the surface of the receptacle which adjoins the sonotrode is flexible in such a way that it deforms to fit up tightly against the active surface of said sonotrode.

In all examples, the sonotrode acts cooperatively with at least one glass bead contained in the sample inside a receptacle.

The diameter of each bead is of between 90 and 150 and preferably of 100 micrometers ($\mu$m) for the lysis of bacteria, and of between 150 and 1500 and preferably of 100 $\mu$m for the lysis of yeast cells. These values are not theoretical and, after extensive research carried out by the applicant, resulted in the submission of patent application PCT/IB98/01475 on Sep. 23, 1998, under French priority of Sep. 23, 1997. The originality of this principle lies in the fact that these values are also applicable to the method of direct sonication.

According to a particularly interesting modified embodiment, the apparatus includes at least two sonotrodes.

Moreover, each receptacle is maintained in physical contact with the sonotrode(s) through a means of pressurization.

Each sonotrode can emit ultrasound at a range of frequencies of between 20 and 50 kHz (more precisely, between 30 and 40 kHz and preferably of close to 35 kHz).

This invention also concerns an ultrasound method for lysing cells in a biological sample contained in a receptacle, which uses at least one sonotrode. According to a first implementation, the method is characterized in that it consists in:

placing the receptacle in direct contact with the active surface of the sonotrode(s), and activating said sonotrode(s) for long enough to lyse the cells in the sample but preserve the DNA and/or RNA molecules released for subsequent operations, e.g. amplification.

According to a second implementation, the method is characterized in that it consists in:

placing the receptacle in direct contact with the active surface of the sonotrode(s), activating said sonotrode(s) for long enough to lyse the cells in the sample and fragment the DNA and/or RNA molecules released in such a way that subsequent operations can be performed, e.g. amplification.

According to a modified embodiment of the two preceding implementations, prior to the activation of the sonotrode (s), the receptacle is compressed up against the active surface of said sonotrode(s).

Each sonotrode is activated in the following way:

a sonication time of 10 to 15 minutes, a cycling ratio of between 40 and 60% (preferably 50%), and an output power of 10 to 30 W.

According to a preferred mode of implementation of the method, activation of each sonotrode corresponds to the emission of a series of pulses each lasting between 5 and 20 seconds, and preferably between 10 and 15 seconds.

The accompanying drawings are given by way of example and are not to be taken as in any way limiting. They are intended to make the invention easier to understand.

Figure 1:
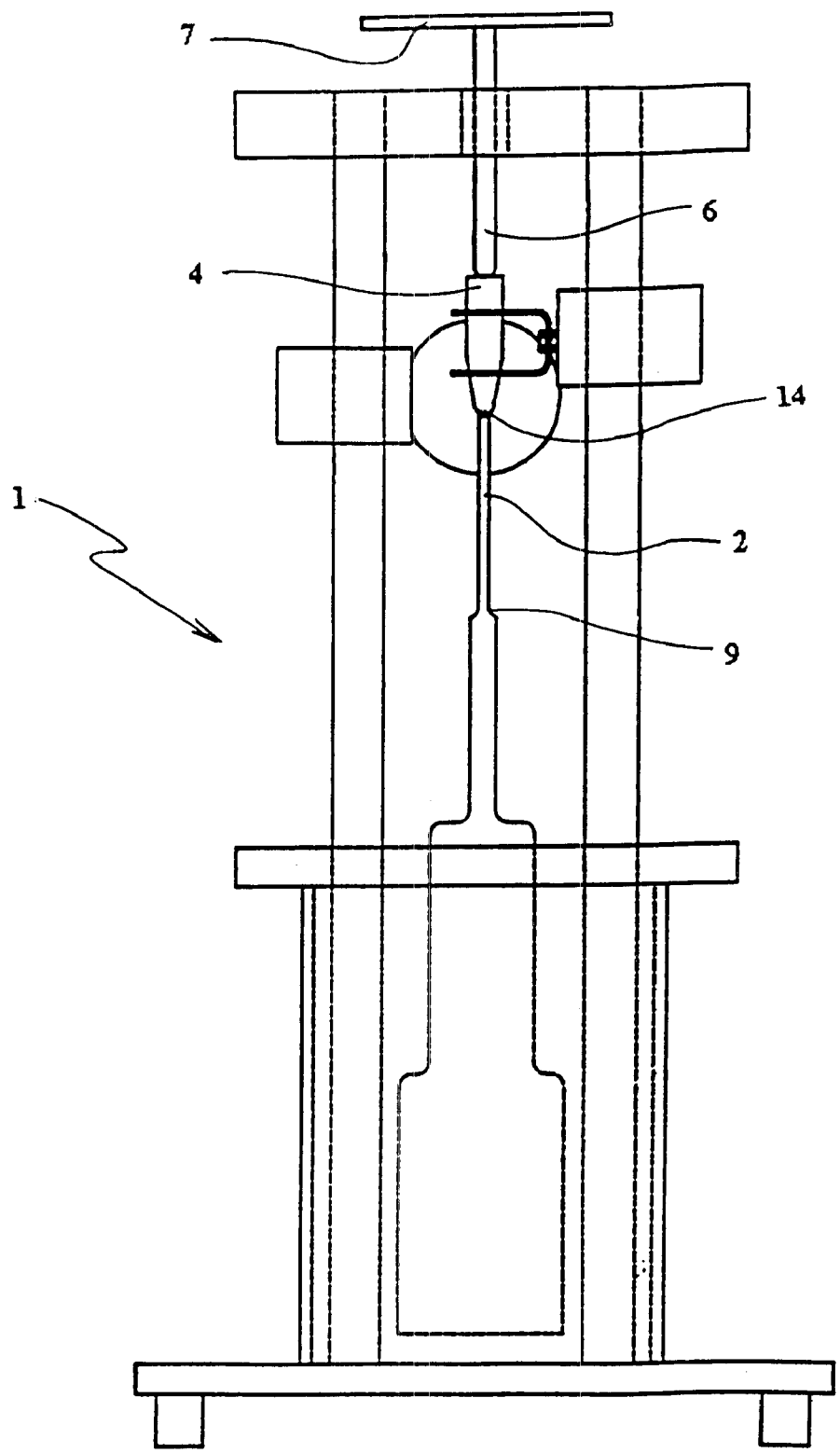
FIG. 1 shows a 20 kHz sonotrode in a configuration for use with a tube.

This invention concerns a device for lysing microorganisms using ultrasound without any coupling liquid between the ultrasound emitter and the biological sample. This device can be used to release nucleic acids while, at the same time, controlling the extent of their fragmentation and maximizing the overall quantity of genetic material released.

Another object of this invention consists in a novel sonication principle, the original feature of which derives from the fact that transduction occurs directly, otherwise referred to as direct sonication. It consists in directly coupling the tube(s) or any other suitable receptacles) containing the sample to be lysed on a sonotrode with a shape which matches that of the tube(s) or receptacle(s). In this case, therefore, there is no coupling liquid.

Yet another object of this invention consists in defining parameters for the sonication which results in efficient lysis of the sample and controlled fragmentation of the nucleic acid molecules released into the medium.

I) VARIOUS EMBODIMENTS OF THE LYTIC APPARATUS

A—First Embodiment:

A first lytic apparatus was evaluated. This type of apparatus (1) is clearly illustrated in FIG. 1.

The apparatus (1) includes a sonotrode (2) (model ViA operating at 20 kHz with a tip diameter of 4 millimeters [mm]). The generator (3) used to excite the sonotrode (2) has an power rating of 300W (BioBlock VibraCell, Model 72401) and can operate in either continuous or pulse mode. Both output power and pulse cycling ratio (10 to 90%) can be varied. The cycling ratio is defined as follows:

Cycling ratio (%)=Ton/(Ton+Toff)

where Ton and Toff define a pulsing profile in which Ton is the length of time during which ultrasound waves are generated, and Toff is the duration of the interval between two Ton periods.

The tube (4) containing a sample to be analyzed (5) acts as the receptacle and is placed on the tip of the ultrasound-generating unit (2). It is kept in place by pressure from the 1t upper plate (6). A weight (7) placed on the plate (6) controls the degree of coupling between the tip of the sonotrode (2) and the tube (4) (depending on the mass of the weight [7]). The tubes (4) used for the tests were Nunc Cryo-type Tubes (1.8 ml) with a round bottom, substantially U-shaped. Other shapes and brands of tubes may also be used.

Once the unit has been assembled, the tube (4) is subjected to ultrasound for varying periods of time, usually between 1 and 15 minutes (min).

Tests showed that, by adjusting the settings of the various parameters (output power, sonication time, cycling ratio, the quantity of glass beads, the coupling weight on the plate, etc., microorganisms could be satisfactorily lysed without damage to the tube and nucleic acids could be preserved-the extent of preservation depending on the settings selected.

Calculating the power density transmitted into the tube (4) makes it possible to evaluate the possibility of tube damage and predict the extent of cavitation.

Power Density $Dp$ (W/cm$^2$)=$Pe$(W)×$\eta$/$Sc$(cm$^2$)

where,

Pe: Electrical Power provided by the generator (in W),
$\eta$: Coefficient for converting Electrical Power into Acoustic Power (dimensionless)
Sc: The area of contact between sonotrode and tube (in cm$^2$)

The incident Electrical Power is usually 20W (15 to 35W tested), and the efficiency of electro-acoustic conversion can be estimated at 80%: therefore, for this apparatus (1), $Dp=20\times0.8/(3.14\times0.2^2)=127$ W/cm$^2$.

Figure 2:
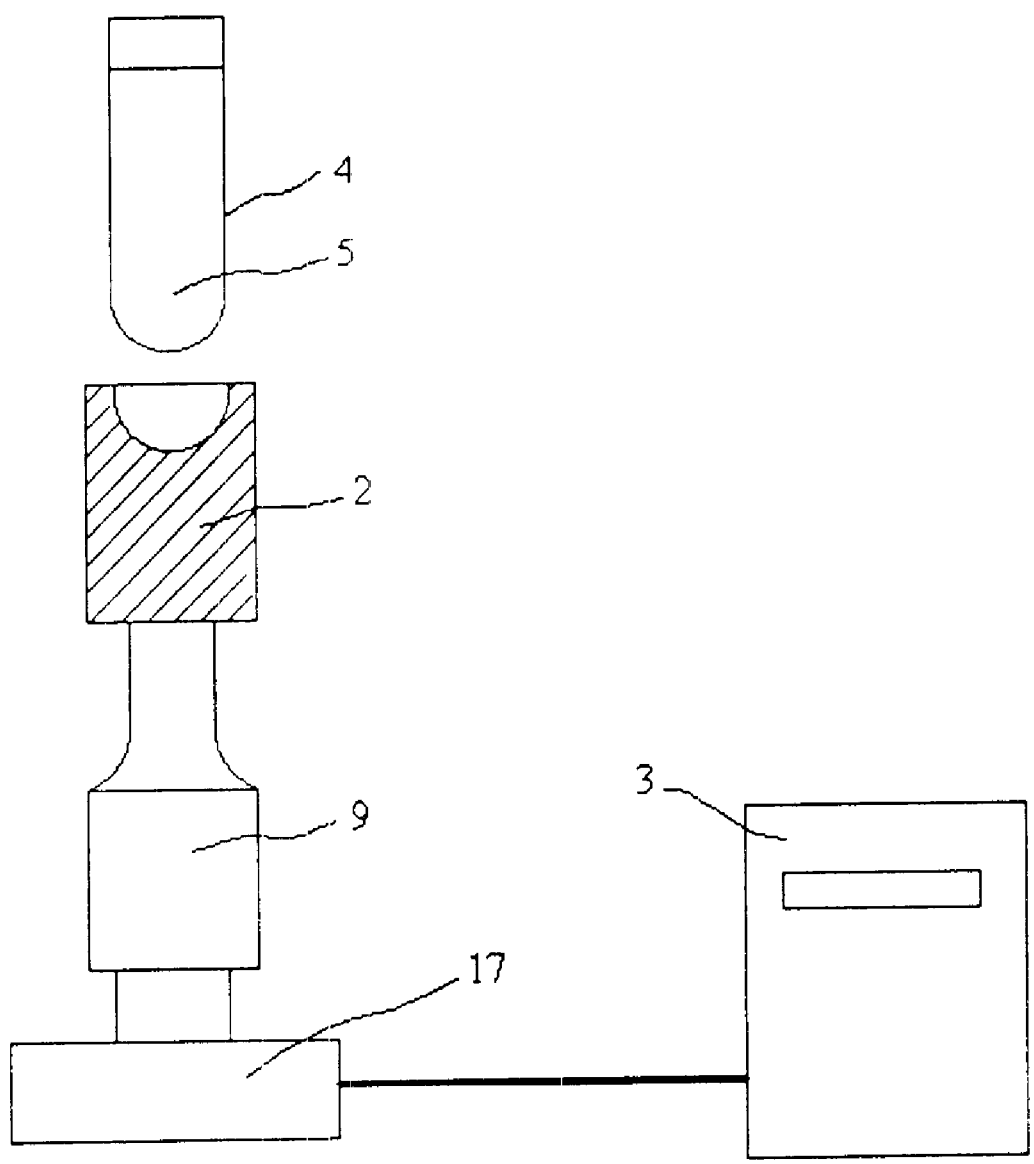
FIG. 2 shows a 35 kHz sonotrode, according to the invention, in a configuration for use with a tube before the tube has been inserted for sonication.

B—Second Embodiment:

A second lytic apparatus (1) was constructed with a direct sonication system operating at 35 instead of 20 kHz. This apparatus (1) is shown in FIG. 2. Although the external structures of both these sonotrodes (operating at 20 and 35 kHz respectively) are identical, the 35 kHz version has a number of advantages.

Firstly, at an equivalent power output, it is associated with less cavitation. The cavitation threshold (i.e. the power output above which cavitation occurs and below which it does not) rises in a substantially parabolic relationship with frequency. Thus, for the same amount of acoustic power delivered, the extent of cavitation is slightly less at 35 kHz than it is at 20 kHz.

Secondly, less of the sample is ejected from the body of the liquid (which phenomenon complicates sample recovery) than is with the 20 kHz sonotrode which has a larger amplitude of vibration.

Thirdly and finally, the system is less cumbersome since the length of the elements which make up the sonotrode (2) decreases as frequency increases.

The power for this sonotrode (2), which operates at 35 kHz, is supplied by a 500W generator (3) (MW 1000 GSIP from Sodeva). The same kind of plate (6) can be used to control the pressure to regulate the coupling between said tube (4) and sonotrode (2).

Whatever the type of sonotrode (20 or 35 kHz), a booster (9) can be used which-depending on its cross-sectional ratio and the position in which it is placed-makes it possible to either amplify or attenuate the amplitude of the vibrations at the tip of the ultrasound-generating unit. This amplification or attenuation is directly proportional to the relative dimensions of the tube (4) or whatever recipient is being used. Thus, by way of example, reducing the diameter of the tube from 15 to 12 mm would increase the amplitude of the vibrations by a factor of 15/12=1.25.

In practice, the booster (9) consists of a metal cylinder made of the same material as the rest of the ultrasound-generating unit, usually titanium or aluminum. The middle portion is regularly tapered. The length of said booster (9) corresponds to half the wavelength of the sound wave for reasons of acoustic adaptation.

The purpose of the booster (9) is to potentiate the amplitude of vibration at the tip of the sonotrode and thereby increase the acoustic power delivered into the medium. Amplification of the vibrations is directly proportional to the ratio between the two different diameters of the booster (9).

FIG. 2 shows various components of the ultrasound-generating unit; the mechanical support structure and the pressure plate (6) are not shown.

In order to estimate the power density, the contact area for one hemisphere has to be calculated, $Sc=2\pi R^2=2\times3.14\times0.6^2=2.26$ cm$^2$ i.e. with 20W of incident electrical power and a conversion factor of 80%, the power density for the second apparatus (1) is given by:

$Dp=20\times0.8/2.26=7.1$ W/cm$^2$ i.e. a power density which is eighteen times lower than that for the first apparatus (1).

The lower power density means that the tube (4) can be submitted to much higher power without damage.

Figure 3:
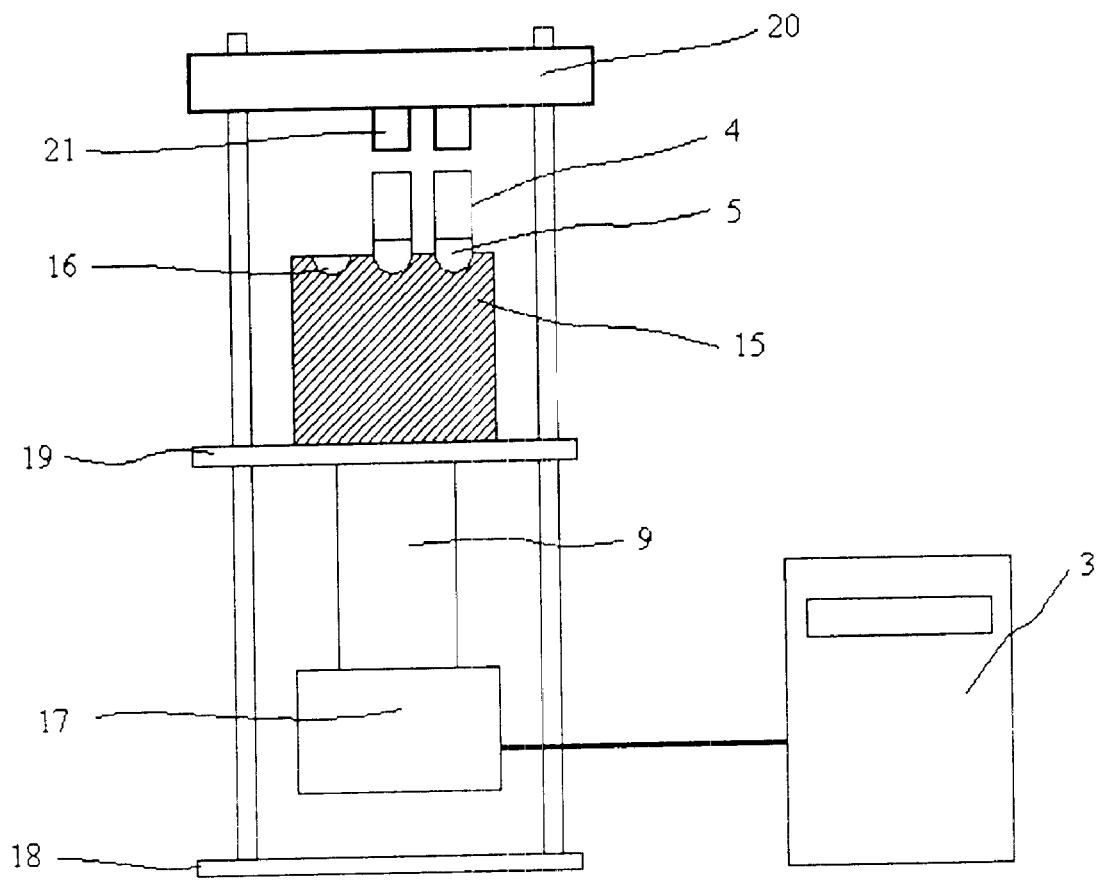
FIG. 3 shows a 35 kHz sonotrode, according to FIG. 2, but which can be used with two different tubes.

C—Third Embodiment:

The method can also be implemented with several tubes (4). Thus, a third embodiment of the apparatus (1) is possible in which the contents of at least two tubes can be lysed simultaneously, as represented in FIG. 3. The frequency is the same as that of the second apparatus, i.e. 35 kHz, and its shape is similar-hemispherical, as described in the following. A spring system makes it possible to adjust the pressure exerted on each individual tube (4) in order to render the coupling force the same for all positions of the sonotrode (2).

II) DIFFERENT EMBODIMENTS OF THE RECEPTACLE CONTAINING THE SAMPLE TO BE PROCESSED

A—First Embodiment:

The first embodiment comprises, of course, an entirely ordinary tube (4) as shown in FIGS. 1 through 3. The shape of the tubes shown in these drawings is not limiting and many other shapes-more and less tapered, with or without at least one truncated portion which may be reversed or not, etc. could be used with the invention.

In this case, the first lytic apparatus (1) would be less efficient than the second. Thus, with the second lytic apparatus, coupling between the sonotrode (2) and the tube (4) is improved by the presence of a concave tip which fits over the U-shaped end of said tube (4). Since acoustic power is transmitted over a more extensive area of contact, a broader range of power can be used without damaging the tube (4) by virtue of Joule Effect dissipation due to too high a power density because the contact area is too small.

Moreover, since the active surface (8) of the sonotrode (2) is U-shaped, the receptacle (4) is maintained in an ideal position with respect to the sonotrode (2) which makes for improved reproducibility between one run and another. With the first apparatus, reproducibility is more difficult to control.

Moreover, this shape also distributes the ultrasound in a far more even pattern and therefore gives more effective turbulence in the receptacle or tube (4). It is possible and even preferable to have beads (9) inside said receptacle (4), in which case the result of lysis is still reproducible.

Figure 4:
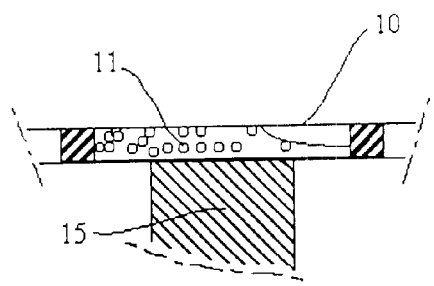
FIG. 4 shows a card in a horizontal position, the contents of which card are lysed by direct sonication according to the invention.
Figure 5:
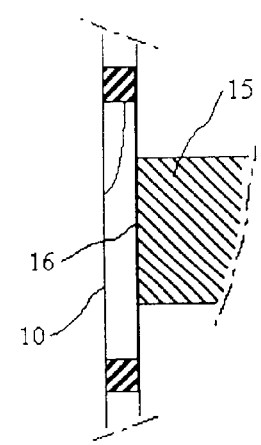
FIG. 5 shows a card in a vertical position, the contents of which card are lysed by direct sonication according to the invention.
Figure 6:
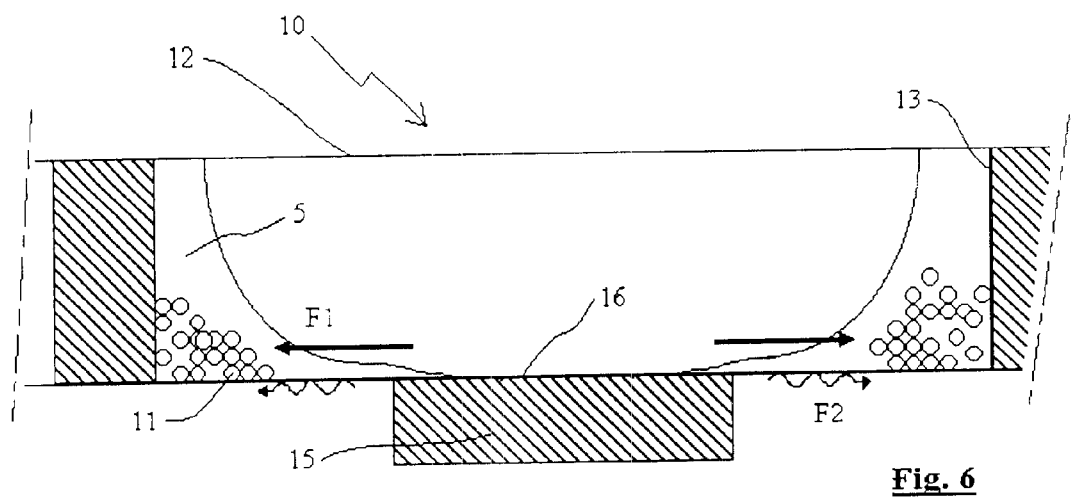
FIG. 6 corresponds to a more detailed representation of FIG. 4 showing how the liquid and the glass beads behave during direct sonication.

B—Second Embodiment:

This embodiment is shown in FIGS. 4 through 6. It concerns a card (10) made of plastic which includes at least one hole or well (13) which crosses the card (10) all the way from one side to the other. The two openings of the well (13) are covered in sheets of film (12) made of some transparent, flexible material which thus define a cavity inside which sonication can be performed.

In this case, the ultrasound-generating unit could be convex in shape so that, when it is applied to one of the sheets of covering film (12), it deforms the film (12) thereby increasing the coupling and enhancing the efficiency of lysis.

Experimental Results

Experiments were carried out on two types of sonotrode, one vibrating at 20 kHz and the other at 35 kHz. These sonotrodes were used with either conventional tubes (commercially available) or consumables in a card format.

In order to evaluate these different sonotrodes, two experimental models were selected:

bacteria (*Staphylococcus epidermidis* as a model system) representing the type of microorganism which is most commonly assayed in test samples.

yeast cells (*Candida krusei* as a model system) which are known to be particularly difficult to lyse and which are also commonly assayed in test samples.

Two different approaches were used for this investigation:

1—The testing of different combinations of the various parameters of sonication in order to identify optimal lysis conditions: lysate analysis consisted in making optical density measurements to estimate the percentage lysis, and performing agarose gel electrophoresis in order to evaluate the release of nucleic acids as well as the extent of their fragmentation. As far as the agarose gel electrophoresis is concerned, no photographs are appended because of the problem of poor xerographic reproduction but all the results are described.

2—Investigation of sensitivity: using the optimal parameter settings as determined in the first stage, determination of the smallest number of microorganisms that can be lysed with subsequent successful nucleic acid amplification and detection, using any amplification method, most notably the PCR.

III) SONICATION BY SONOTRODES IN TEST TUBES

A—20 kHz Sonotrode

The device used in these experiments is fully described in Section I-A "First embodiment" of the lytic apparatus, and is clearly illustrated in FIG. 1. Therefore, this device includes a generator supplying a 20 kHz sonotrode on which is placed a lysis tube and a weight to insure contact between sonotrode and tube.

1°) Determination of Ideal Parameter Settings:

Yeast cells (*Candida krusei*) were directly sonicated using the above-described device, with a series of variations of the various parameters of sonication; the objective was to maximize the efficiency of lysis and nucleic acid release, and to minimize the fragmentation of the nucleic acids.

Operating Conditions:

For all experiments, the acoustic power was between $Ps=0.8\times25=20W$ and $Ps=0.8\times35=28$ W. In both cases, the conversion factor $\eta$ was 80%. It can be considered that the overall amount of energy delivered into the tube was similar in all the different experiments. Output power is only adjusted to generate sufficient turbulence when a larger quantity of beads is being used.

The fixed parameters were as follows:

20 kHz sonotrode with a 300W Bioblock generator, a weight of 1430 g and Nunc tubes (1.8 ml), the sample was a suspension of yeast cells (*Candida krusei*, strain n° 9604058 from the bioMérieux collection) at a density of about $10^7$ cells/ml (OD [550 nm]=0.600) in buffer (pH=8.5) containing 80 mM HEPES, 1 mM EDTA and 2% lithium lauryl sulfate, sample volume=600 μl, and glass beads with a diameter of between 425 μm and 600 μm (acid-washed, Sigma).

Variable Parameters are Listed in Table 1:

output power=Ps (in Watts), cycling ratio (in percentage), sonication time (in minutes), and quantity of glass beads (in microliters).

Results were evaluated by:

observation of the movement of the beads which should be neither too limited (no movement) nor too vigorous (associated with excessive warming up of the sample), and analysis of a 20 μl aliquot of the lysate by agarose gel (0.8%) electrophoresis, staining with ethidium bromide (EB) and identification of nucleic acid molecules released in an intact form (chromosomal DNA, and 18S and 26S RNA) using a molecular weight marker.

TABLE 1

Direct sonication using a 20 kHz sonotrode and lysis of yeast cells in the tube: the impact of acoustic power, cycling ration and the quantity of glass beads on bead movement and on the release of yeast nucleic acids
Results:

| Conditions n° | P (W) | Cycling ratio (%) | Time (mn) | Quantity of beads (μl) | Results Movement | Nucl. acids |
|---|---|---|---|---|---|---|
| 1 | 24 | 20 | 5 | 30 | (+) | – |
| 2 | 24 | 20 | 5 | 60 | + | (+) |
| 3 | 23 | 50 | 5 | 30 | + | + |
| 4 | 20 | 50 | 5 | 60 | + | ++ |
| 5 | 21 | 80 | 5 | 60 | + | (+) |
| 6 | 28 | 80 | 2 | 90 | + | (+) |

Bead movement: (+) weak, +correct

Release of intact nucleic acids: –none, (+) visible, ++visible and intense

Two tests were performed for each different experimental condition.

The results show that:
- the movement of the glass beads can be exactly controlled by adjusting the power delivered into the tube (Ps),
- yeast cells can be lysed to release their nucleic acids in an unfragmented form: there are signals (in the form of bands) on the agarose gel corresponding to chromosomal DNA and to ribosomal RNA species (notably under conditions n° 3 and 4), and
- parameter settings have a direct impact on the amount of nucleic acid released and on the way in which it is fragmented:
  - cycling ratio: too low a setting (20%) fails to release adequate material, too high a setting (80%) similarly generates low signals, in this case due to excessive nucleic acid fragmentation, and
  - quantity of beads: with a larger quantity of beads (60 ml rather than 30 μl) and the correct degree of movement, more material is released.

The conditions selected as ideal for subsequent experiments are therefore those listed as conditions n° 4 in Table 1.

2°) Investigation of Sensitivity:

Sensitivity was investigated using a range of yeast suspensions containing between $10^7$ and $10^2$ yeast organisms per test. These cells were directly sonicated in the optimal conditions as identified in the first series of experiments. For comparison, the same series of suspensions was processed using a reference method, namely vortexing, as described in the applicant's patent application FR97/12164.

Operatina Conditions:

After preparation of yeast suspensions at densities of $10^2$, $10^3$, $10^4$ and $10^5$ cells/test in water, they were treated by:
- direct sonication: conditions described above in Table 1 (conditions n° 4),
- vortexing: a Falcon tube (5 ml) containing a 600 μl aliquot of the sample, 150 μl of glass beads (diameter=425–600 μm, three glass beads (diameter=2 mm) and five iron beads (diameter=1.5 mm); vortexed for 12min at maximum power.

Lysates were purified over Sephadex G-50 columns (Quick Spin Columns for DNA Purification from Boehringer Mannheim) in accordance with the manufacturer's instructions, and then a 10μl aliquot of the lysate was amplified using the PCR according to the method of Makimura et al (*J. Med. Microbiol.*, 1994; 40: 358–364). A 20 μl aliquot of the PCR product was subsequently analyzed by agarose gel (1.2%) electrophoresis and stained with ethidium bromide (EB).

TABLE 2

Direct sonication using a 20 kHz sonotrode and the lysis of yeast cells in the tube: sensitivity of PCR detection of yeast after two different lysis procedures
Results:

| yeast organisms detected | $10^e7$ | $10^e6$ | $10^e5$ | $10^e4$ | $10^e3$ | $10^e2$ |
|---|---|---|---|---|---|---|
| lysis by direct sonication | ++ | ++ | ++ | + | − | − |
| lysis by vortexing | ++ | ++ | ++ | + | − | − |

The two different lysis procedures were the following:
lysis by direct sonication using a 20 kHz sonotrode, and lysis by vortexing.

Signal on the gel:—none, +visible, ++visible and intense

Two tests were performed for each different experimental condition.

The results show that:
- lysates generated by direct sonication in optimal conditions 1I could be amplified using the PCR: intense bands were seen which corresponded to the size of the expected PCR product, and
- after lysis by both direct sonication and vortexing, the sensitivity of this PCR method was $10^4$ yeast cells/test. Therefore, lysis by sonication gives the same efficiency as a reference lysis method.

3°) Conclusions:

These experiments showed direct sonication at 20 kHz to be a feasible lysis method. They also showed that sonication parameters can be adjusted to maximize the amount of yeast nucleic acids released and minimize the extent of their fragmentation. Finally, these parameters make it possible to release nucleic acids which are suitable for PCR amplification and to attain a level of sensitivity equivalent to that of a reference lysis method.

B—35 kHz Sonotrode:

The sonication device used in these experiments is fully described in Section I-B "Second embodiment" of the lytic apparatus and clearly illustrated in FIG. 2. The advantages of sonication at 35 kHz over that at 20 kHz were also explained in the same section. Moreover, this lytic device affords a greater area of contact between tube and sonotrode; the advantages of this were detailed in Section II-A "First embodiment" of the receptacle containing the sample to be treated.

1°) Determination of Ideal Parameter Settings:

The objective was identify sonication parameters for maximum efficiency of lysis of bacteria and yeast cells, and maximum nucleic acid release coupled with minimum fragmentation.

Operating conditions:

For the following experiments, acoustic power is defined by the amplitude of the vibration of the ultrasound waves generated by the sonotrode. This amplitude is given as a percentage of the power of the generator which supplies the sonicator with electrical energy.

The fixed parameters were as follows:
- 35 kHz sonotrode with a 500W Sodeva generator, a weight of 1430 g, and Nunc tubes (1.8 ml),
- sample:
  - for the yeast tests: a suspension of yeast cells (*Candida krusei*, strain n° 9604058 from the bioMérieux collection) at a density of about $2.10^7$ cells/ml ($OD_{550nm}=0.950$) in buffer (pH=8.5) containing 80mM HEPES, 1 mM EDTA and 2% lithium lauryl sulfate, and
  - for the bacterial tests: a bacterial suspension (*Staphylococcus epidermidis*, strain n° A054 from the bioMérieux collection) at a density of about $10^9$ bacteria/ml ($OD_{550nm}=0.900$) in a buffer (pH=7.2) containing 30 mM Tris, 5mM EDTA and 100 mM NaCl,
- sample volume=600 μl, and
- glass beads:
  - for the yeast tests: 90 μl of beads (diameter=425 μm–600 μm) (acid-washed, Sigma), and
  - for the bacterial tests: 120 μl of beads (diameter=106 μm) (VIA I).

Variable parameters are listed in Tables 2 and 3:
- amplitude of vibration (in percentage),
- output power=Ps (in Watts) (which is directly proportional to the amplitude), the duration of the ultrasound pulses (Ton) and the interval between pulses (Toff) (in minutes), these time factors defining the cycling ratio: Ton/(Ton+Toff), and overall sonication time (in minutes).

Results were evaluated by:

observation of the movement of the beads, recording of the optical density at 550 nm of the cell suspensions before and after lysis. The approximate percentage lysis was determined by:

($OD_{550nm}$ after lysis)/(($OD_{550nm}$ before lysis)×100), and analysis of a 20 µl aliquot of the lysate by agarose gel (0.8%) electrophoresis, staining with ethidium bromide (EB) and identification of nucleic acid molecules released in an intact form (chromosomal DNA, and 18S and 26S RNA) using a molecular weight marker. Fragmented nucleic acids appear below these bands.

Output power 20W (amplitude 80%): more violent commotion, the beads undergoing larger displacements and occupying a greater volume of the liquid. In parallel, the heating of the liquid is increased.

The results pertaining to bead movement show that:

an output power of 15W is sufficient to generate adequate commotion in the glass beads, compared with the 20 kHz sonotrode, the 35 kHz model does not need as high a power output to generate adequate movement of the glass beads (15 W as opposed to 20W), and this is so for a larger quantity of beads (90 µl and 120 µl as opposed to 60 µl), and because the ultrasound is being transmitted over a greater area (the entire bottom of the tube), the commotion induced in the beads is more even and the liquid is heated up to a lesser extent.

The results pertaining to lysis show that:

the bacteria and yeast cells were lysed and their nucleic acids were released,

TABLE 3

Direct sonication using a 35 kHz sonotrode and the lysis of yeast cells in the tube: the impact of acoustic power, cycling ratio and sonication time on the percentage of yeast cells lysed, as well as on the release of nucleic acids and the extent of their fragmentation
Results: Yeast tests

| Conditions | Ampl. | Ps | Ton | Toff | Duration | lysis | Results | | |
|---|---|---|---|---|---|---|---|---|---|
| | | | | | | | | nucleic acids | |
| n° | (%) | (W) | (sec) | (sec) | (min) | (%) | ADN | rARN | Fragmented |
| 1 | 50 | 15 | 10 | 10 | 10 | 15% | ++ | ++ | 0 |
| 2 | 50 | 15 | 10 | 10 | 15 | 19% | ++ | +++ | 0 |
| 3 | 50 | 15 | 10 | 2 | 10 | 27% | ++ | + | 0 |
| 4 | 80 | 20 | 10 | 10 | 10 | 26% | ++ | + | 0 |

Release of nucleic acid: −none, +visible, ++visible and intense, +++visible and highly intense Two tests were performed for each different experimental condition.

parameter settings have a direct impact on the amount of nucleic acid released and on the way in which it is fragmented:

Power:

TABLE 4

Direct sonication using a 35 kHz sonotrode and the lysis of bacteria in the tube: the impact of acoustic power, cycling ratio and sonication time on the percentage of bacteria lysed, as well as on the release of nucleic acids and the extent of their fragmentation
Results: Bacterial tests

| Conditions | Ampl. | Ps | Ton | Toff | Duration | lysis | Results | | |
|---|---|---|---|---|---|---|---|---|---|
| | | | | | | | | nucleic acids | |
| n° | (%) | (W) | (sec) | (sec) | (min) | (%) | ADN | rARN | fragmented |
| 1 | 50 | 15 | 10 | 10 | 10 | 30% | 0 | ++ | ++ |
| 2 | 50 | 15 | 10 | 10 | 15 | 49% | 0 | ++ | ++ |
| 3 | 50 | 15 | 10 | 2 | 10 | 40% | 0 | ++ | ++ |
| 4 | 80 | 20 | 10 | 10 | 10 | 53% | 0 | + | ++ |
| 5 | 80 | 20 | 10 | 10 | 15 | 59% | — | — | +++ |

Release of nucleic acid: −none, +visible, ++visible and intense, +++visible and highly intense Two tests were performed for each different experimental condition.

Results Pertaining to Bead Movement:

Output power 15W (amplitude 50%): regular commotion of the beads in the bottom half of the liquid volume creating a dome-shaped collision zone in the middle. The beads are displaced small distances and impact on one another.

(amplitude) a high amplitude of vibration (80%) means that it is possible to increase to a small extent the percentage lysis and the amount of nucleic acids released, but this is associated with heavy fragmentation.

an amplitude of 50% releases enough of the nucleic acids at the same time as leaving all the chromosomal DNA intact as well as some of the ribosomal RNA, Cycling ratio: a high cycling ratio (Ton 10 sec/ Toff 10 sec) has the same effects as high amplitude, Sonication time: long sonication times (e.g. 15 min) make it possible to increase the percentage lysis and the amount of nucleic acids released without affecting the extent to which they are fragmented, the condition adopted for insuring the release of as much nucleic acid as possible in an unfragmented form is a long sonication time with relatively low amplitude and cycling ratio settings (conditions n° 2, Tables 2 and 3), and the condition adopted for insuring the release of as much nucleic acid as possible in a heavily fragmented form is a long sonication time with a high amplitude (conditions n° 5, Table 2).

2°) Investigation of Sensitivity:

Sensitivity was investigated using a range of yeast suspensions containing between 106 and 102 yeast organisms per test. The yeast cells were directly sonicated under the various conditions evaluated in the first part:

1. the condition adopted for insuring the release of as much nucleic acid as possible in an unfragmented form,
2. this same condition, but simply increasing the cycling ratio,
3. still condition n° 1, but with an increased amplitude.

In the first part, it was shown that these latter two conditions resulted in a higher percentage lysis but also heavier nucleic acid fragmentation. In parallel, the same range of suspensions was processed using a reference lysis method, namely vortexing as described in the applicant's patent application FR97/12164.

Ooeratina Conditions:

After preparation of yeast suspensions at densities of $10^2$, $10^3$, $10^4$ and $10^5$ cells/test in water, they were treated by:

direct conditions n° 1, 2 and 3 as stipulated in the first part (Tables 2 and 3) sonication:

vortexing:a Falcon tube (5 ml) containing a 600 µl aliquot of the sample, 150 µl of glass beads (diameter=425–600 µm), three glass beads (diameter=2 mm, and five iron beads (diameter=1.5 mm); vortexed for 12 min at maximum power.

Lysates were purified over Sephadex G-50 columns (Quick Spin Columns for DNA Purification from Boehringer Mannheim) following the manufacturer's instructions, and then a 10 µl aliquot of the lysate was amplified using the PCR according to the method of Makimura et al (*J. Med. Microbiol.*, 1994; 40: 358–364). A 20 µl aliquot of the PCR product was subsequently analyzed by agarose gel (1.2%) electrophoresis and stained with ethidium bromide (EB)

TABLE 5

Direct sonication using a 20 kHz sonotrode - sensitivity of PCR detection of yeast after different lysis procedures
Results:

| yeast organisms detected | $10^6$ | $10^5$ | $10^4$ | $10^3$ | $10^2$ |
|---|---|---|---|---|---|
| lysis by direct sonication n° 1 | 106 | 105 | + | – | – |
| lysis by direct sonication n° 2 | 0 | 0 | (+) | – | – |
| lysis by direct sonication n° 3 | 0 | 0 | (+) | – | – |
| lysis by vortexing | 0 | 0 | + | (+) | – |

The different lysis procedures were:

lysis by direct sonication using a 20 kHz sonotrode operating in three different sets of conditions, and
lysis by vortexing.

Signal on the gel: –non visible, (+) weak, +visible, ++visible and intense

Two tests were performed for each different experimental condition.

The results show that:

lysates generated by direct sonication in optimal conditions could be amplified using the PCR with intense bands seen on the agarose gel corresponding to the size of the expected PCR product, after lysis by direct sonication in three different sets of conditions, as few as $10^4$ yeast cells per test could be detected by PCR; however, the signal given by $10^4$ yeast cells is weaker when the conditions for the sonication step tend to promote heavier nucleic acid fragmentation (conditions n° 2 and 3), and the sensitivity of detection observed following lysis by sonication is very close to that obtained after lysis using a reference method, namely vortexing.

3°) Conclusions:

These experiments showed direct sonication at 35 kHz to be a feasible lysis method for two different types of microorganism (bacteria and yeast). It was also shown that astute setting of certain key sonication parameters will maximize lysis of these microorganisms at the same time as allowing control of the extent of fragmentation of the released nucleic acids. These key sonication parameters have been identified and the ideal settings have been determined. In addition, it has been shown that lysis by direct sonication at 35 kHz yields nucleic acids that can be amplified by PCR, and that the lysis conditions identified as compatible with PCR amplification give a level of sensitivity of detection which is very close to that obtained with a reference lysis method, namely vortexing. Sonication conditions which tend to induce heavy nucleic acid fragmentation are slightly less compatible with PCR amplification. Nevertheless, nucleic acid fragmentation may have a very positive action in a number of applications in molecular biology, e.g. the isolation of specific nucleic acids by hybridization.

C—Multi-tube 35 kHz Sonotrode:

The concept of simultaneous, direct sonication of several tubes is shown in FIG. 3 and is described in Section I-C "Third embodiment" of the lytic apparatus. The following experiments were carried out using a device in which twelve tubes can be sonicated at the same time. Otherwise, it has the same characteristics as the 35 kHz sonotrode used for the experiments described in Section I-B (same sonication frequency, same area of contact between tube and sonotrode, etc.). The special feature of this multi-tube sonication device is the fact that it allows individual adjustment of the pressure exerted on each of the twelve tubes in order to insure reproducible tube-sonotrode contact for every one and thus guarantees consistent and effective lysis from one tube to another.

1°) Adjustment of Tube-sonotrode Coupling to Guarantee Reproducible Sonication:

The pressure being exerted on each of the twelve tubes by the weight was measured and adjusted to insure that the pressure on each tube was the same. The evenness of the pressure was confirmed by observation of the same type of bead movement in each tube during sonication under the optimal conditions as determined in Section I-B.

Operating Conditions:

The force applied to each tube was measured using a disk-shaped force sensor (reference BC302 3KG MV/V from C2AI, France) (diameter=16 mm, thickness=4.5 mm) positioned on a truncated tube in such a way that the height of the sensor tube plus the thickness of the sensor was equivalent to the height of the sample-containing tubes. The force sensor was connected to a digital display (48×96 programmable type from C2AI, France) so that the pressure reading corresponding to the compression force could be recorded.

For the measurements, eleven tubes containing sample and the sensor tube were inserted in the twelve positions on the sonotrode. The sensor tube together with the force sensor was successively moved from position 1 to position 2, then to position 3, etc. up till position 12 in order to measure the force applied to the tubes in each position. Three series of measurements were made. The standard deviation of the distribution of the coupling force calculated from the means of the three series of measurements revealed that, before adjustment, there was great disparity, with a Coefficient of Variation (CV) of the order of 10% (see Table 6).

With the sensor in place, the force exerted at each position was then adjusted using the compression spring at each pressure plane.

After adjustment, the CV for the compression forces had been reduced to under 1%.

TABLE 6

Direct sonication with a multi-tube 35 kHz sonotrode - the pressure exerted on the various tubes
Results:

| Position | Force (series 1) | Force (series 2) | Force (series 3) | Mean | After adjustment (24/12) |
|---|---|---|---|---|---|
| 1 | 0.625 | 0.595 | 0.605 | 0.608 | 0.573 |
| 2 | 0.575 | 0.567 | 0.572 | 0.571 | 0.577 |
| 3 | 0.595 | 0.595 | 0.604 | 0.598 | 0.574 |
| 4 | 0.606 | 0.609 | 0.592 | 0.602 | 0.563 |
| 5 | 0.684 | 0.694 | 0.684 | 0.687 | 0.572 |
| 6 | 0.651 | 0.659 | 0.659 | 0.656 | 0.573 |
| 7 | 0.5 | 0.508 | 0.527 | 0.512 | 0.572 |
| 8 | 0.502 | 0.519 | 0.513 | 0.511 | 0.579 |
| 9 | 0.484 | 0.494 | 0.494 | 0.491 | 0.571 |
| 10 | 0.552 | 0.523 | 0.518 | 0.531 | 0.571 |
| 11 | 0.582 | 0.569 | 0.571 | 0.574 | 0.572 |
| 12 | 0.526 | 0.556 | 0.548 | 0.543 | 0.572 |
| Mean | 0.574 | 0.574 | 0.574 | 0.574 | 0.572 |
| Standard deviation (%) | 11.0 | 10.6 | 10.2 | 10.5 | 0.7 |

Characterization of Lysis-inducing Movement:

After equalization of the pressure being exerted on each of the twelve tubes, it was visually confirmed that the movement of the beads during sonication was more or less comparable. Sonication was carried out exactly as described in Section III-B, conditions n° 2 described in Tables 3 and 4 (determined as optimal for maximum lysis and preservation of nucleic acid integrity) with water as the "sample". Subsequently, the weight acting on the twelve tubes was gradually increased (from 2.7 kg to 3.7 kg, then to 4.6 kg and finally to 5.6 kg) to enhance the contact between the tubes and the sonotrode.

It was observed that insufficient weight (2.7 kg) resulted in a great deal of variability between different tubes in terms of the movement of the beads. In practice, this weight is not enough to insure adequate contact between the twelve tubes and the sonotrode since the beads in some of the tubes were barely moving at all.

In contrast, above a certain threshold (3.7 kg), the beads in all twelve tubes moved in a comparable way: regular commotion of the beads in the bottom half of the liquid volume creates a dome-shaped collision zone in the middle. The beads were displaced small distances and impacted on one another.

2°) Conclusions:

It was shown that the principle of direct sonication at 35 kHz with an optimal area of contact between tube and sonotrode (described in Section I-B) can be extended to the simultaneous treatment of several tubes. Moreover, it is possible to obtain reproducible lysis-inducing movement in all the tubes by adjusting the force governing tube-sonotrode contact. These two observations demonstrate that it would be possible to exploit the principle of direct sonication in an automatic analyzer to treat a certain number of samples in a reproducible way.

IV) SONICATION BY SONOTRODES FOR CONSUMABLES IN A CARD FORMAT 20 kHz Sonotrode for Cards:

The card sonication device is shown in FIGS. 4 through 6. These figures show two alternative configurations as well as how the liquid and the beads behave during sonication. The sonotrode used for this device is the same as that described in Section I-A "First embodiment" of the lytic apparatus but with a flat tip with a diameter of 13 mm. The consumable in a card format is described in Section II-B "Second embodiment" of the receptacle containing the sample to be treated. This consumable is made of polystyrene (although other plastics which are compatible with biological tests may be used) and its dimensions are 40×40×4 mm. For introduction of the sample and the glass beads, the card has a circular opening (of variable diameter) in the middle which is referred to as the well. The bottom of the well is constituted by either a 0.3 mm layer of plastic or by a sheet of adhesive polypropylene film. The film also serves to close the consumable.

1°) Evaluation of Parameters Specific to the Card Format:

Only those parameters specifically dependent on the card format were evaluated with fixed values assigned for the other sonication parameters which had already been investigated (see Section I-A). Lysis experiments were carried out with bacteria and yeast cells, and both the efficacy of lysis and the extent of nucleic acid fragmentation were determined.

Operating Conditions:

The fixed parameters were as follows:

20 kHz sonotrode with a 300W Bioblock generator and the consumable as described above with the card in a horizontal position, power:
  for the yeast tests: 25 W, and
  for the bacterial tests: 13–14 W, a cycling ratio of 80% and a sonication time of 5 min, sample:
  1. for the yeast tests: a suspension of yeast cells (*Candida krusei*, strain n° 9604058 from the bioMérieux collection) at a density of about $2.10^7$ cells/ml ($OD_{550nm}$=0.950) in buffer (pH=8.5) containing 80 mM HEPES, 1 mM EDTA and 2% lithium lauryl sulfate, and
  2. for the bacterial tests: a bacterial suspension (*Staphylococcus epidermidis*, strain n° A054 from the bioMérieux collection) at a density of about $8,5×10^8$ bacteria/ml ($OD_{550nm}$=0.720) in the same buffer, and glass beads:
1. for the yeast tests: glass beads (diameter=425 µm–600 µm) (acid-washed, Sigma), and
2. for the bacterial tests: glass beads (diameter=106µm) (VIA I).

Variable parameters are listed in Tables 6 and 7:
the diameter of the well (in millimeters),
the nature of the bottom of the well (plastic bottom or a flexible, transparent film),
the volume of the sample (in microliters), and
the volume of glass beads (in microliters).

Results were evaluated by:
observation of the movement of the beads, and
analysis of a 20 µl aliquot of the lysate by agarose gel (0.8%) electrophoresis, staining with ethidium bromide (EB) and identification of nucleic acid molecules released in an intact form (chromosomal DNA, and 18S and 26S RNA) using a molecular weight marker.
Fragmented nucleic acids appear below these bands.

Rlease of nucleic acid: −none, +visible, ++visible and intense
NB: for conditions n° 3 and 4, the sonication time was 10 min.

Results Pertaining to Bead Movement:
Horizontal position with flexible film bottom: the ultrasound waves generated by the sonotrode push the liquid and the beads out to the edge of the well (see FIG. 6). The beads are displaced small distances and impact on one another. This commotion is mainly due to the ultrasound which is transmitted laterally by the film. The film does not get damaged and the liquid does not heat up to any significant extent.

Horizontal position with a plastic bottom: the liquid and beads occupy the same position as above but the movements of the beads are clearly attenuated. In contrast, there is intense heating of the plastic bottom of the well and, in consequence, of the liquid.

Vertical position with flexible film bottom: the liquid and beads accumulate at the bottom of the well, right opposite the sonotrode in a smaller volume than when the card is in

TABLE 7

Direct sonication using a 20 kHz sonotrode, lysis of bacteria in a card: the impact of parameters which are specific to the "card" format (well size, nature of the bottom, sample volume and quantity of beads) on bacterial lysis, and on the quantity of nucleic acids released and the extent of their fragmentation.
Results: Bacterial tests

| | "Card" parameters | | | | Results nucleic acids | | |
|---|---|---|---|---|---|---|---|
| Conditions n° | diameter (mm) | bottom | volume (µl) sample | volume (µl) beads | DNA | rRNA | fragmented |
| 1 | 15 | film | 200 | 60 | + | ++ | − |
| 2 | 15 | plast. | 200 | 60 | − | + | + |
| 3 | 20 | film | 300 | 90 | + | ++ | − |
| 4 | 20 | plast. | 300 | 90 | − | + | + |
| 5 | 25 | film | 600 | 180 | + | + | − |
| 6 | 25 | plast. | 600 | 180 | + | + | + |
| 7 | 30 | film | 900 | 180 | (+) | (+) | − |
| 8 | 30 | plast. | 900 | 180 | + | (+) | − |

Release of nucleic acid: −none, +visible, ++visible and intense
NB: for conditions n° 8, the card was in a vertical position.

a horizontal position. The movements of the beads is vigorous but there is no significant heating of the liquid.

The results show that:

TABLE 8

Direct sonication using a 20 kHz sonotrode, lysis of yeast cells in a card: the impact of parameters which are specific to the "card" format (well size, nature of the bottom, sample volume and quantity of beads) on the lysis of yeast cells, and on the quantity of nucleic acids released and the extent of their fragmentation.
Results: Yeast tests

| | "Card" parameters | | | | Results nucleic acids | | |
|---|---|---|---|---|---|---|---|
| Conditions n° | diameter (mm) | bottom | volume (µl) sample | volume (µl) beads | DNA | rRNA | fragmented |
| 1 | 15 | film | 600 | 30 | + | + | − |
| 2 | 15 | plast. | 300 | 30 | (+) | (+) | (+) |
| 3 | 30 | film | 600 | 180 | + | ++ | − |
| 4 | 30 | plast. | 600 | 180 | − | (+) | (+) | the bacteria and yeast cells were lysed and their nucleic acids were released, sonication with the card in a horizontal position and with a well bottom comprising a flexible film gives highly effective lysis and releases a large amount of nucleic acids (very intense signals on the gel) without any fragmentation of either DNA or ribosomal RNA. In practice, the extremely thin, strong and flexible film provides good coupling between sonotrode and film. Therefore, the beads are vigorously impelled and the ultrasound is transmitted with limited Joule Effect dissipation so there is little heating. Moreover, confinement of the liquid to the edge of the well-out of the acoustic axis-significantly reduces the phenomenon of cavitation in the liquid, sonication with a plastic well bottom not only releases much less nucleic acid but also induces heavy fragmentation of both DNA and rRNA. This is clearly due to the weaker movements of the beads and the major heating of the bottom of the card and hence of the liquid. Both these phenomena are explained by poor coupling between the sonotrode and the rigid bottom of the card as well as a greater Joule Effect, and the greater the diameter of the well, the less effective is the lysis and the lower the amount of nucleic acid released. Distancing of the liquid and beads from the sonotrode at the center is therefore to be avoided since this diminishes the effect of the ultrasound. Therefore, it is recommended that cards with wells with a diameter close to that of the sonotrode be used.

2°) Conclusions:

It has been clearly shown that direct sonication in a consumable in a card format is feasible. These experiments have also identified usage conditions for highly effective lysis and perfect preservation of the integrity of the released nucleic acids (specifically, a well diameter close to that of the sonotrode and coupling provided by a thin, flexible film). Preserving the integrity of nucleic acids is extremely important in the techniques of molecular biology which often require perfectly intact nucleic acid molecules. Moreover, the use of this type of consumable for direct sonication is of particular interest because other processing operations and tests could be carried out on the same sample in the same card. In this way, the lysis of microorganisms as well as their analysis and identification could all be carried out in one single consumable which would both reduce the risk of cross-contamination between samples and also make for easy automation of the entire procedure.

REFERENCES

1. Apparatus
2. Sonotrode or ultrasound-generating unit
3. Generator
4. Tube or receptacle
5. Sample contained in the tube (4) or card (10)
6. Means of pressurization or upper plate
7. Ballast weight
8. Active surface of the sonotrode (2)
9. Booster
10. Card or receptacle
11. Glass beads:
12. Films
13. Well
14. Flat tip
15. Sonotrode or ultrasound-generating unit
16. Active surface of the sonotrode (15)
17. Transducer
18. Base
19. Support plate
20. Pressure plate
21. Compression component associated with a tube (4)
F1. Direction of displacement of the sample (5)
F2. Vibrations of the film (12).

What is claimed is:

1. An apparatus, including a sonotrode designed to generate ultrasound of variable power in at least one biological sample containing cells to be lysed, the sample being contained in at least one receptacle suited to that purpose, the sonotrode being in direct contact with said receptacle containing the sample to be lysed without any fluid between surfaces of contact between the sonotrode and receptacle, wherein the sonotrode has an active surface which fits with the shape of the outer surface of all or part of each receptacle containing the sample to be lysed; the active surface of the sonotrode in contact with the receptacle is concave in shape.

2. An apparatus including a sonotrode designed to generate ultrasound of variable power in at least one biological sample containing cells to be lysed, the sample being contained in at least one receptacle suited to that purpose, the sonotrode being in direct contact with the receptacle containing the sample to be lysed without any fluid between surfaces of contact between the sonotrode and receptacle, wherein the sonotrode has an active surface which fits with the shape of the outer surface of all or part of each receptacle containing the sample to be lysed; the active surface of the sonotrode in contact with the outer surface of the receptacle is convex in shape.

3. The apparatus of claim 1, wherein the surface of the receptacle which synergizes with the sonotrode is flexible in such a way that it fits tightly up against the active surface of said sonotrode.

4. The apparatus of claim 1, wherein the sonotrode synergizes with at least one glass bead present in the sample contained in the receptacle.

5. The apparatus of claim 1, wherein each bead has a diameter of between 90 and 150 and preferably of 100 micrometers ($\mu$m) for the lysis of bacteria, and a diameter of between 150 and 1500 and preferably of 500 $\mu$m for the lysis of yeast cells.

6. The apparatus of claim 1, wherein it includes at least two sonotrodes.

7. The apparatus of claim 1, wherein each receptacle is in physical contact with the sonotrode through the action of a means of pressurization.

8. The apparatus of claim 1, wherein each sonotrode has an ultrasound emission frequency of between 20 and 50 kHz, more precisely of between 30 and 40 kHz and preferably of close to 35 kHz.

9. An ultrasound-based method for lysing cells in a biological sample contained in a receptacle, which uses at least one sonotrode, comprising:

placing the receptacle in direct contact with a concave or convex active surface of the sonotrode, and activating said sonotrode for long enough to lyse the cells in the sample but preserve the DNA and/or RNA molecules released for subsequent operations.

10. An ultrasound-based method for lysing cells in a biological sample contained in a receptacle, which uses at least one sonotrode, comprising:

placing the receptacle in direct contact with a concave or convex active surface of the sonotrode, and activating said sonotrode for long enough to lyse the cells in the sample but fragment the DNA and/or RNA molecules released for subsequent operations.

11. The method of claim 9, wherein prior to activation of the sonotrode, the receptacle is compressed against the active surface of said sonotrode.

12. The method of claim 9, wherein each sonotrode is activated under the following conditions:

a sonication time of 10 to 15 minutes, a cycling ratio of between 40 and 60% and preferably 50%, and an output power of 10 to 30W.

13. The method of claim 12, wherein the activation of each sonotrode corresponds to a series of pulses lasting between 5 and seconds, and preferably between 10 and 15 seconds.

* * * * *

UNITED STATES PATENT AND TRADEMARK OFFICE
CERTIFICATE OF CORRECTION

PATENT NO.    : 6,686,195 B1
DATED         : February 3, 2004
INVENTOR(S)   : Bruno Colin et al.

It is certified that error appears in the above-identified patent and that said Letters Patent is hereby corrected as shown below:

Title page,
Item [75], Inventors, change "Lyons" to -- Lyon -- (both occurrences).

Column 22,
Line 3, change "5 and seconds" to -- 5 and 20 seconds --.

Signed and Sealed this

Sixth Day of July, 2004

JON W. DUDAS
*Acting Director of the United States Patent and Trademark Office*